(12) United States Patent
Monfaredi et al.

(10) Patent No.: US 9,289,265 B2
(45) Date of Patent: Mar. 22, 2016

(54) MRI-COMPATIBLE, INTEGRATED FORCE AND TORQUE SENSORS AND SYSTEMS THAT INCORPORATE THE SENSORS

(71) Applicant: The Johns Hopkins University, Baltimore, MD (US)

(72) Inventors: Reza Monfaredi, Hyattsville, MD (US); Iulian Ioan Iordachita, Lutherville, MD (US); Reza Seifabadi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 142 days.

(21) Appl. No.: 13/939,041

(22) Filed: Jul. 10, 2013

(65) Prior Publication Data

US 2015/0018840 A1     Jan. 15, 2015

(51) Int. Cl.
*G01R 33/20* (2006.01)
*G01L 5/16* (2006.01)
*A61B 19/00* (2006.01)
*A61B 17/00* (2006.01)

(52) U.S. Cl.
CPC .............. *A61B 19/20* (2013.01); *A61B 19/201* (2013.01); *G01L 5/166* (2013.01); *A61B 19/2203* (2013.01); *A61B 2017/00911* (2013.01); *A61B 2019/466* (2013.01); *A61B 2019/5236* (2013.01)

(58) Field of Classification Search
CPC .......... G01L 5/16; G01R 33/20; A61B 19/00; A61B 19/201; A61B 2019/5236; A61B 19/2203; A61B 2019/466; A61B 2017/00911
USPC .............. 73/862.331–862.335, 800, 862.041; 600/411; 707/2, 713, 758; 606/130
See application file for complete search history.

(56) References Cited

U.S. PATENT DOCUMENTS

| 5,950,185 | A | 9/1999 | Alon et al. |
| 7,987,177 | B2 | 7/2011 | Beyer et al. |
| 2003/0050555 | A1* | 3/2003 | Critchlow et al. ............. 600/420 |
| 2006/0206127 | A1* | 9/2006 | Conquergood et al. ........ 606/180 |

(Continued)

OTHER PUBLICATIONS

Alon et al., "The space complexity of approximating the frequency moments," Journal of Computer and System Sciences, vol. 58, 1999.

(Continued)

*Primary Examiner* — Laura Martin
*Assistant Examiner* — Suman K Nath
(74) *Attorney, Agent, or Firm* — Venable LLP; Henry J. Daley; Laura G. Remus

(57) ABSTRACT

A magnetic resonance imaging (MRI) compatible sensor for measuring torque with respect to an axis of rotation in conjunction with an applied linear force includes a shaft arranged in a longitudinal direction substantially along the axis of rotation, a base component arranged along the axis of rotation and displaced with respect to the shaft, a torque detector assembly configured to be coupled to rotational motion of the shaft about the axis of rotation relative to the base component, and a linear-force detector assembly configured to be coupled to linear motion of the shaft from a force applied in a direction substantially coincident with the axis of rotation relative to the base component. The torque detector assembly and the linear-force detector assembly are substantially de-coupled from each other such that torque measurements are substantially independent of linear force measurements. The MRI compatible sensor consists essentially of MRI compatible materials.

25 Claims, 13 Drawing Sheets

(56) References Cited

U.S. PATENT DOCUMENTS

| | | | | |
|---|---|---|---|---|
| 2009/0054908 | A1* | 2/2009 | Zand et al. | 606/130 |
| 2009/0192980 | A1 | 7/2009 | Beyer et al. | |
| 2010/0298826 | A1* | 11/2010 | Leo et al. | 606/41 |
| 2011/0160745 | A1* | 6/2011 | Fielding et al. | 606/130 |
| 2012/0143044 | A1* | 6/2012 | Govari | A61M 25/0108 600/421 |
| 2012/0265051 | A1* | 10/2012 | Fischer | A61B 10/0241 600/411 |
| 2013/0190734 | A1* | 7/2013 | Taylor et al. | 606/1 |
| 2013/0317519 | A1* | 11/2013 | Romo | A61B 19/2203 606/130 |

OTHER PUBLICATIONS

Chapuls et al., "Design of a Simple MRI/fMRI Compatible Force/Torque Sensor." Proceedings of 2004 IEEE/RSJ International Conference on Intelligent Robots and Systems. 3, 2593-2599(2004).

Charikar et al., "Finding frequent items in data streams," Theoretical Computer Science, vol. 312, 2004, pp. 3-15.

Hill et al., "Fiber Bragg grating technology fundamentals and overview," Journal of Lightwave Technology, 15(8), 1263-1276 (1997).

Iordachita et al., "A sub-millimetric, 0.25 mN resolution fully integrated fiber-optic force-sensing tool for retinal microsurgery," Int J CARS, 4(4). 383-390 (2009).

Polygerinos et al., "Novel Miniature MRI-Compatible Fiber-Optic Force Sensor for Cardiac Catheterization Procedures," IEEE International Conference or Robotics and Automation, 2598-2603 (May 2010).

Puangmali et al., "Novel Design of a 3-Axis Optical Fiber Force Sensor for Applications in Magnetic Resonance Environments," IEEE International Conference on Robotics and Automation, 3682-3687 (2009).

Seifabadi et al., "Accuracy study of a robotic system for MRI-guided prostate needle placement," International Journal of Medical Robotics and Computer Assisted Surgery, 7(2), 181-190, (Jun. 2012).

Seifabadi et al., "Design of a teleoperated needle steering system for MRI-guided prostate interventions", 4th IEEE RAS & EMBS International Conference on Biomedical Robotics and Biomechatronics (BioRob), 793-798 (Jun. 2012).

Su et al., "A 3-Axis Optical Force/Torque Sensor for Prostate Needle Placement in Magnetic Resonance Imaging Environments," IEEE International Conference on Technologies for Practical Robot Applications, 5-9 (2009).

Tada et al., "Development of an optical 2-axis force sensor usable in MRI environments," Proc. of the IEEE Sensors, 2, 984-989 (2002).

Tada et al., "Design of an MRI-compatible three-axis force sensor," IEEE/RSK International Conference on Intelligent Robots and Systems, 3505-3510 (2005).

Tan et al., "Triaxial MRI-Compatible Fiber-optic Force Sensor," IEEE Transactions on Robotics,27(1), 65-74 (Feb. 2011).

Tokuda et al., "Preclinical evaluation of an MRI-compatible pneumatic robot for angulated needle placement in transperineal prostate interventions," Int JCARS, 7(6), 949-957, (Jun. 2012).

Tokuno et al., "High-Precision MRI-Compatible Force Sensor with Parallel Plate Structure," Proceedings of the 2nd Biennial IEEE/RAS-EMBS International Conference on Biomedical Robotics and Biomechatronics. 33-38 (2008).

Park et al., "Real-Time Estimation of Three-Dimensional Needle Shape and Deflection for MRI-Guided Interventions," IEEE/ASME Trans. Mechatronics-Focused Section on Surgical and Interventional Medical Devices, 15(6), 906-915 (Dec. 2010).

* cited by examiner

MRI-COMPATIBLE, INTEGRATED FORCE AND TORQUE SENSORS AND SYSTEMS THAT INCORPORATE THE SENSORS

FEDERAL FUNDING BY THE U.S. GOVERNMENT

This invention was made with Government support of Grant No. 2 R01 CA111288-06, awarded by the Department of Health and Human Services, The National Institutes of Health (NIH). The U.S. Government has certain rights in this invention.

BACKGROUND

1. Field of Invention

The field of the currently claimed embodiments of this invention relates to force and torque sensors, and more particularly to magnetic resonance imaging (MRI) compatible, integrated force and torque sensors.

2. Discussion of Related Art

In the last decade, robot assisted MRI-guided prostate needle placement has gained a lot of interest due to the superior imaging capabilities of MRI systems. An MRI-compatible, integrated force and torque sensor could be an important part of robotic systems for prostate percutaneous interventions under MRI, for example.

An example of teleoperated needle steering under real-time MRI guidance is provided in [1]. The clinician interacts with a master robot which is placed next to the scanner and therefore must be MRI-compatible. The slave robot which is installed on the base robot [2], [3] (the base robot orients the needle toward the target), follows the motions of the master. (See also US 2012/0265051 A1, the entire contents of which are incorporated herein by reference.)

Slave and master have two degrees-of-freedom (2 DOF) each, linear motion for the needle plus the rotation of it. Since the needle is beveled, the combination of these two motions enables needle steering. Visual feedback is provided by real-time MRI. A controller enables communication between master and slave. The idea of teleoperation is to enable the surgeon to remotely perform the task while the patient is inside the scanner for real-time imaging.

Since the master robot uses piezo motors for the sake of MRI-compatibility and ease of control, it is non-backdrivable. Therefore, a 2 DOF force-torque sensor is required to enable movement. In addition, for feedback of the needle insertion force to the clinician's hand, a force sensor should be placed at the slave side behind the needle. Both force sensors should be MRI-compatible. MRI-compatibility for sensors means that: 1) the sensor should be able to operate in a high magnetic field and 2) it has minimal disturbance to the MRI images. This means that usage of any ferromagnetic parts should be reduced to a minimum, and non-magnetic metallic parts should be avoided. In addition, it implies that the conventional strain gauges should be avoided since they distort the magnetic field and the RF pulse emitted by the scanner thus drastically degrading the image quality. Shielding of strain gauges does not resolve the image degradation.

In previous studies, hydrostatic pressure, differential light intensity, differential optic fiber, optical micrometry, and absolute light intensity have been proposed as alternatives to the conventional strain gauges [4]. Tada et al. [5] developed an optical t-axis force sensor without any metal and electronic components in the sensing element using photo sensors and optical fibers. The sensor was a 2DOF sensor which measures forces in x and y directions and it was rather bulky since it used photo sensors.

Chapuis et al. [6] designed a simple and efficient torque sensor based on light intensity measurement over optical fibers. This sensor allowed the electronic components to be placed outside the scanner room. The sensitivity of transverse torque was reduced to 0.03% of the desired output torque by using a self-guiding flexible structure and optimal mirror placement. This sensor was a single DOF sensor for torque sensing and utilized optical technology for compactness and sensitivity to precise placement of the mirrors.

A MRI-compatible three-axis force sensor was developed in [7]. Differential measure of light intensity is used to develop this sensor using a new MRI-compatible optical micrometry. Optoelectronic devices and pairs of fiber optics are used to measure forces in three directions. Two micrometers were aligned in orthogonal directions in order to realize three-axis force sensitivity.

A parallel plate structure was used to develop a MRI-compatible optical force sensor. It utilized optical micrometry based on differential measures of light intensity [8]. The sensor's head component was made of glass fiber reinforced poly-ether-ether-ketone to reduce axial interference and hysteresis behavior of plastic resin. This was a 1DOF sensor for axial force sensing.

An optical fiber sensing method was designed and fabricated in [9]. The sensor was based on an optical sensing principle and measured forces by deforming a 3 DOF flexible structure. By using an optical sensing scheme, minute deflection of the structure was detected and then the magnitude and direction of the applied force was determined. This sensor measured only forces, and it was bulky because of the sensing principal.

Polygerinos et al. in [10] presented a prototype design and development of a small MRI-compatible fiber optic force sensor for force sensing during MRI-guided cardiac catheterization. A fiber optic cable interrogated a reflective surface at a predefined distance inside a catheter shaft based on light intensity modulation.

Tan et al. have developed a 3DOF axial force sensor with small coupling effects between DOFs. The use of materials with hysteretic behavior made it necessary to use Prandtl-Ishlinskii theory to address this behavior. The sensor was very bulky [11].

Hao Su et al. [4] developed a sensor for two DOF torque measurement and one DOF force measurement. This sensor is based on fiber optic and spherical mirror technology. The sensor was bulky and was not able to measure axial torque which is necessary for needle steering in prostate intervention.

Iordachita et al. designed and analyzed a force measurement device that measures distal forces interior to the sclera using FBGs embedded in a 0.5 mm diameter tool shaft. Utilizing FGB technology in this design made the device as small as possible which was necessary for retinal microsurgery. This device is can be used for force sensing in 2 directions, especially for microsurgery procedures [12].

Despite the advances reported recently concerning MRI-compatible systems, a useful MRI-compatible sensor is still a challenging task. Therefore, there remains a need for improved MRI-compatible, integrated force and torque sensors.

SUMMARY

A magnetic resonance imaging (MRI) compatible sensor for measuring torque with respect to an axis of rotation in conjunction with an applied linear force according to an embodiment of the current invention includes a shaft arranged in a longitudinal direction substantially along the axis of rotation, a base component arranged along the axis of rotation and displaced with respect to the shaft, a torque detector assembly configured to be coupled to rotational motion of the shaft about the axis of rotation relative to the base component, and a linear-force detector assembly configured to be coupled to linear motion of the shaft from a force applied in a direction substantially coincident with the axis of rotation relative to the base component. The torque detector assembly and the linear-force detector assembly are substantially de-coupled from each other such that torque measurements are substantially independent of linear force measurements. The MRI compatible sensor consists essentially of MRI compatible materials.

An MRI-compatible surgical system according to an embodiment of the current invention includes a teleoperated surgical tool system configured to be inserted at least partially within a main coil region of an MRI system, and a control system configured to communicate with the teleoperated surgical tool system. The control system includes a user interface for manual input from a user for real-time control of the teleoperated surgical tool system during imaging of a subject with the MRI system. The MRI-compatible surgical system further includes a signal processing system configured to communicate with the control system during imaging of a subject with the MRI system. At least one of the teleoperated surgical tool system or the control system includes an MRI-compatible sensor for measuring torque with respect to an axis of rotation in conjunction with, and substantially independently of, an applied linear force.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Many clinical procedures involve needle insertion into soft tissue. When high resolution imaging is needed, magnetic resonance imaging (MRI) is the first choice. Accurate needle insertion into soft tissue under MRI requires in-room robot-assisted (master/slave system) intervention and possibly needle steering. The master and slave require the use of MRI-compatible force and torque sensors for control and needle-to-tissue interaction force monitoring, respectively.

A sensor according to an embodiment of the current invention can provide a solution for both master and slave. A decoupled 2-DOF MRI-compatible sensor according to an embodiment of the current invention measures axial torque and force. It can be compact, sensitive, noise free, readily sterilizable, and low cost. Also it can provide temperature compensated measurements and allow for simplified calibration procedures.

Figure 1A:
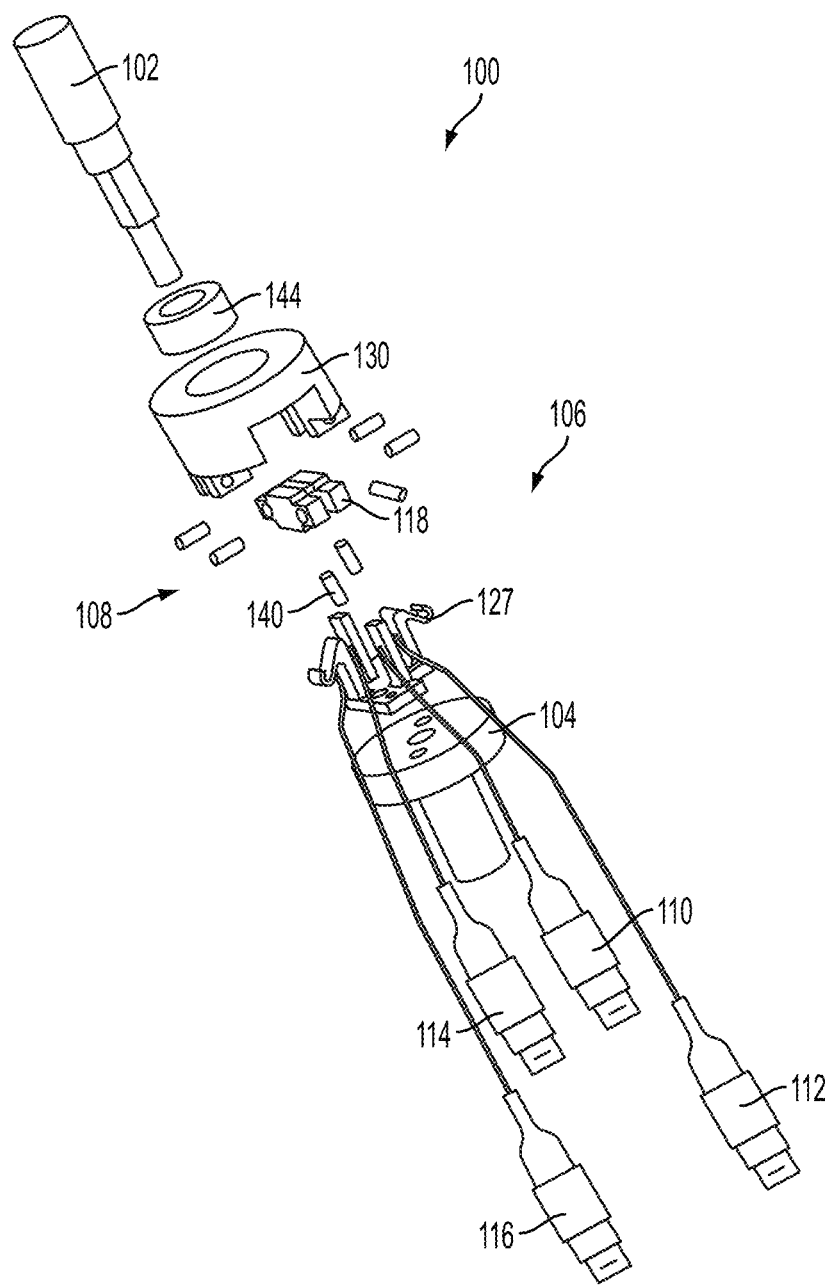
FIG. 1A is an exploded view of an MRI-compatible sensor according to an embodiment of the current invention.
Figure 1B:
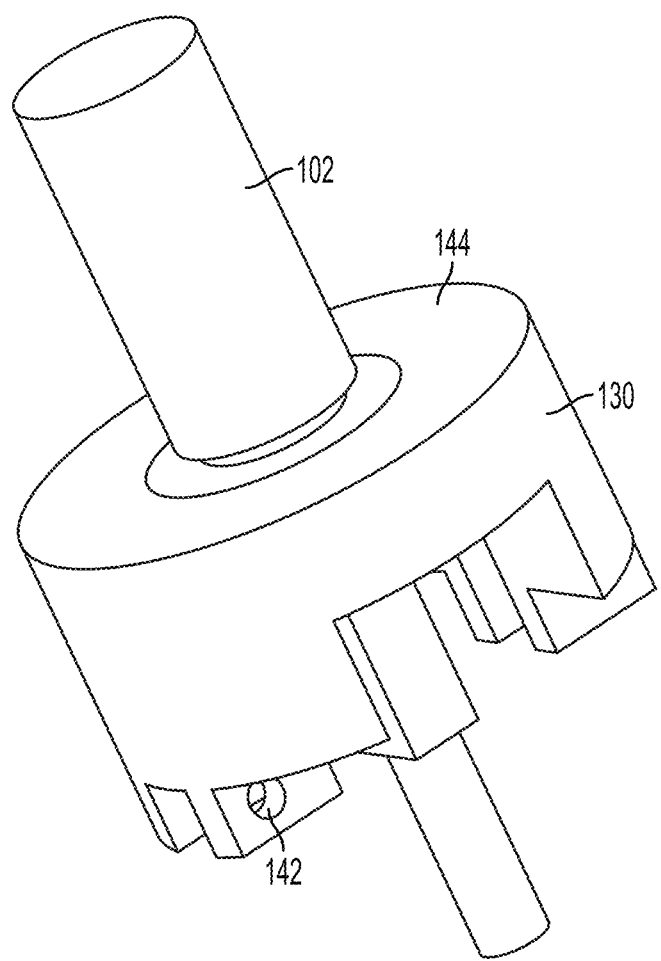
FIG. 1B is an enlarged view of some components shown in FIG. 1A.
Figure 1C:
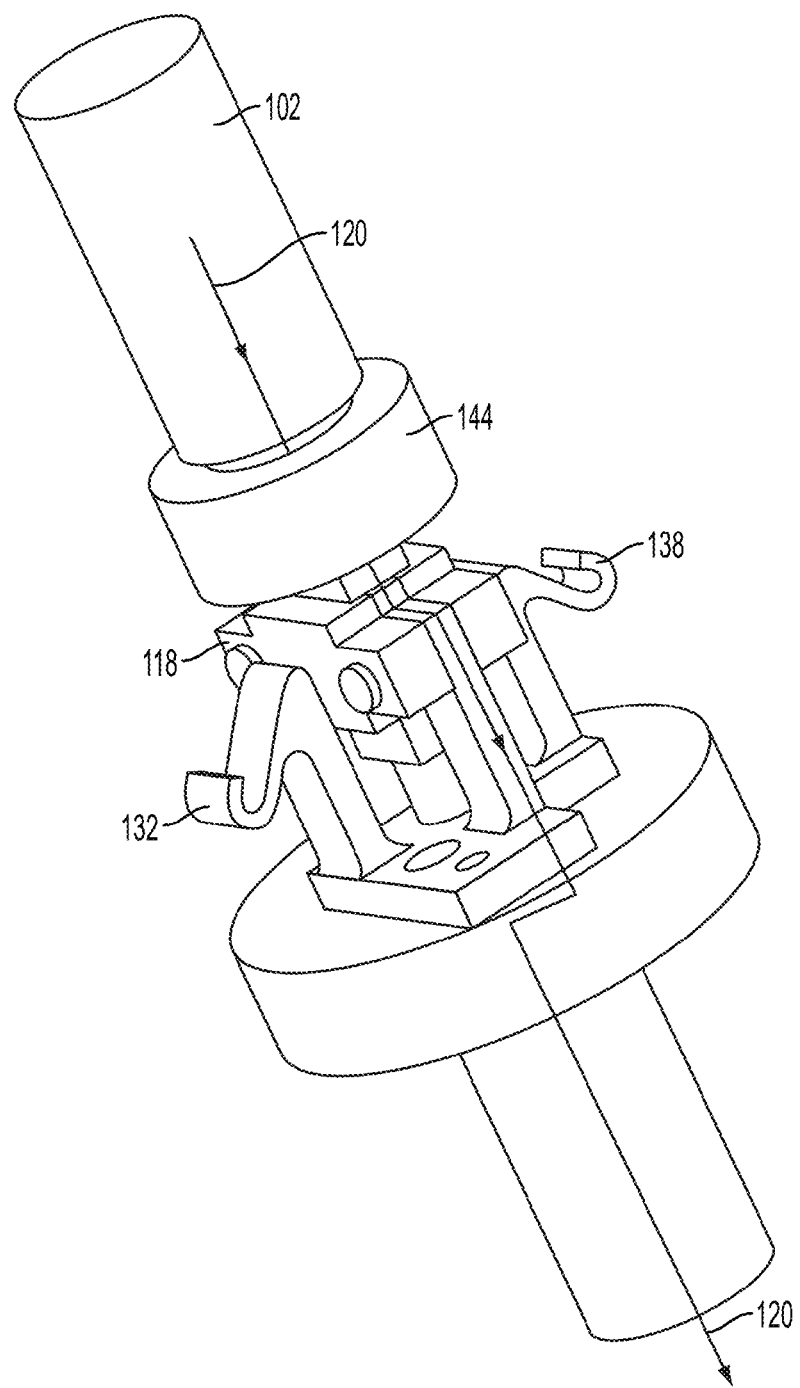
FIG. 1C is a partially assemble view of the MRI-compatible sensor shown in FIG. 1A.

FIG. 1A provides an "exploded" view of a magnetic resonance imaging (MRI) compatible sensor 100 for measuring torque with respect to an axis of rotation in conjunction with an applied linear force according to an embodiment of the current invention. The MRI-compatible sensor 100 includes a shaft 102 arranged in a longitudinal direction substantially along the axis of rotation (axial direction), a base component 104 arranged along the axis of rotation and displaced with respect to the shaft 102, a torque detector assembly 106 configured to be coupled to rotational motion of the shaft 102 about the axis of rotation relative to the base component, and a linear-force detector assembly 108 configured to be coupled to linear motion of the shaft 102 from a force applied in a direction substantially coincident with the axis of rotation relative to the base component 104. The torque detector assembly 106 and the linear-force detector assembly 108 are substantially de-coupled from each other such that torque measurements are substantially independent of linear force measurements. In addition, the MRI compatible sensor 100 is made from MRI compatible materials.

In some embodiments, the torque detector assembly 106 includes a first fiber-optic strain sensor element 110, and the linear-force detector assembly 108 includes a second fiber-optic strain sensor element 112. In further embodiments, the torque detector assembly 106 can include a third fiber-optic strain sensor element 114 arranged relative to the first fiber-optic strain sensor element 110 to provide substantially temperature-independent torque measurements, and the linear-force detector assembly 108 can include a fourth fiber-optic strain sensor element 116 arranged relative to the second fiber-optic strain sensor element 112 to provide substantially temperature-independent linear force measurements. In some embodiments, each of the first, second, third and fourth fiber-optic strain sensors can be an optical fiber comprising a Fiber Bragg Grating (FBG) section.

FIGS. 1B, 1C, 2A and 3A show some of the components of the MRI compatible sensor 100 in more detail. The torque detector assembly 106 includes a rotational engaging component 118 configured to couple to the shaft 102 while the shaft 102 is subjected to a torque along the axis of rotation. The torque transfer 120 is represented schematically in FIG. 1C. The torque detector assembly 106 further includes a flexural beam 122 having a first end 124 (FIG. 2B) fixed relative to the base component 104 and an end 126 free to move relative to the base component 104. (It is incorporated into active element 127 in this embodiment.) The torque detector assembly 106 is not limited to only one flexural beam 122. In the embodiment of FIGS. 1A, 1C, 2A, 2B, 3A, 3B and 3C, there is a second flexural beam 128 (see FIG. 2A). Additional flexural beams could be included in further embodiments. The rotational engaging component 118 is arranged to come into contact with the flexural beam 122 (and also 128) to change an amount of torsion imposed on the flexural beam 122 responsive to the torque along the axis of rotation.

The linear-force detector assembly 108 includes a force-transfer component 130 (FIGS. 1A and 1B) configured to couple to the shaft 102 while the shaft 102 is subjected to a force along the axial direction. The linear-force detector assembly 108 further includes a flexural lever 132 having a first end 134 fixed relative to the base component 104 and an end 136 free to move relative to the base component 104. The force-transfer component 130 is arranged to come into contact with the flexural lever 132 to change an amount of force imposed on the flexural lever 132 responsive to the force along the axial direction. In some embodiments, there can be a second flexural lever 138. Other embodiments could include more than two flexural levers. The linear-force detector assembly 108 further includes a pin 140 to be inserted in holes 142 in the force-transfer component 130. Similarly, than can be a pin for each flexural lever. The pin 140 is positioned to slide along the upper surface of the laterally extending (sloping and curving) portion of the flexural lever 132 to thereby increase or relieve stress on the flexural lever resulting from a change in axial force.

The force-transfer component 130 also includes a rotational slip joint 144 in which the shaft 102 passes through the rotational slip joint 144 such that rotations of the shaft 102 are substantially frictionless so that substantially no torque is transmitted from the shaft 102 to the force-transfer component 130. In some embodiments, the rotational slip joint 144 can be a ball bearing assembly, for example.

FIGS. 4-6B show various views of an actual MRI-compatible sensor 100 according to an embodiment of the current invention.

In operation, application of torque so as to rotate shaft 102 transfers torque to the rotational engaging component 118, which in turn increases (or decreases) force to the flexural beam 122. An FBG attached along one side of the flexural beam 122 either stretches or relaxes, depending on the position of the beam and the direction of the applied torque (i.e., direction of rotation). As the spacing of the pattern of periodic variations of refractive index in the FBG changes, a corresponding change in a reflected optical signal along the optical fiber provide a signal to determine the applied torque. If two FBGs are attached to the beam such that one stretches while the other relaxes due to the applied torque, the two signals can be used to correct for changes in temperature. This is the case since both FBGs will be at substantially the same temperature. Therefore, changes in the spacing of the gratings of the two FBGs due to temperature changes will be substantially the same and thus can be subtracted from the combined signals.

The rotation of the shaft 102 resulting from applied axial torque leaves the force-transfer component 130 substantially unaffected due to the rotational slip joint 144, which can be a ball bearing assembly. On the other hand, an axial force applied to the shaft 102 results in contact with the force-transfer component 130 to transfer a linear force. As the force-transfer component 130 is pushed downward, for example, the pin 140 slide down the upper surface of the torsional lever 132 to cause it to flex, imposing a strain. The rotational engaging component 118 is slidable along the flexural beam 122, thus allowing sensing of linear force without coupling with the torque sensing components. Consequently, the axial torque and the axial linear force measurements are decoupled in the sense that they can be measured independently without one having a significant effect on the other.

Similar to the torque measurements, a FBG is attached to the flexural lever 132 to respond to the imposed strain. Similarly, two FBGs can be used for temperature compensation by placing them on flexural lever 132 such that on stretches while the other relaxes. In the embodiment of FIG. 1A, there are two flexural beams and two flexural levers for a 2 DOF decoupled, integrated torque-axial force sensor. In that embodiment there are four optical fibers with corresponding FBGs, but placed on the four total flexural components in such a way that temperature compensation can be achieved. One could use eight optical fibers with corresponding FBGs in such a design, if desired; however, the reduction to four eliminates some cost, complexity and bulk while improving sensitivity over attaching four FBGs to just a total of two flexural components. Different numbers of fibers could be used without departing from the general concepts of the current invention.

Although the embodiment above describes a 2 DOF corresponding to one torque DOF and one linear force DOF (axial), other embodiments can include 3 DOF and 4 DOF sensors in which one DOF is an axial torque and the other degrees of freedom are components of linear force. For example, the linear-force detector assembly 108 could include flexural levers oriented substantially parallel to flexural beams so that non-axial components of force could be determined by combinations of signals from the plurality of flexural levers. The broad concepts of the current invention are intended to cover such further embodiments.

Figure 7A:
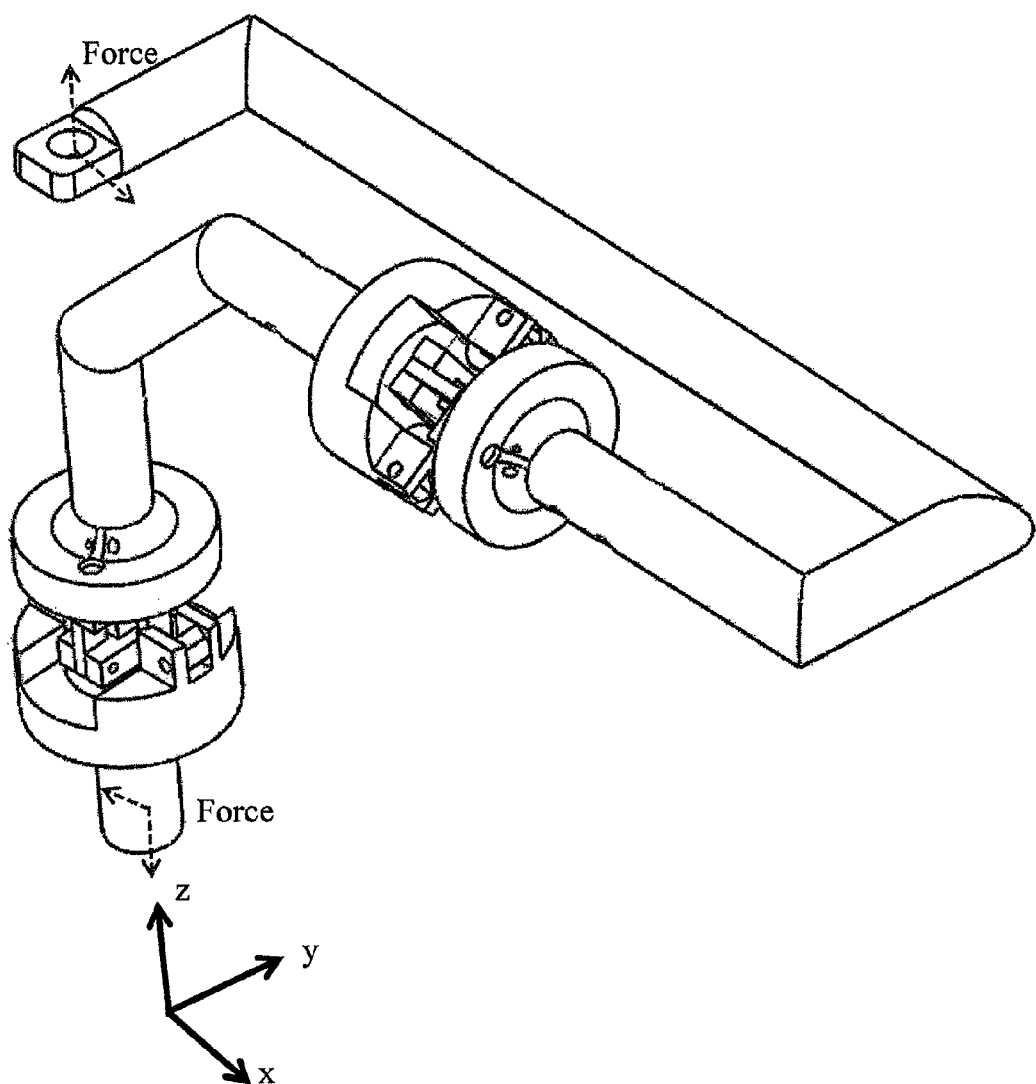
FIGS. 7A and 7B are illustrations of 4 DOF and 6 DOF sensors that combine a plurality of 2 DOF sensors according to an embodiment of the current invention.
Figure 7B:
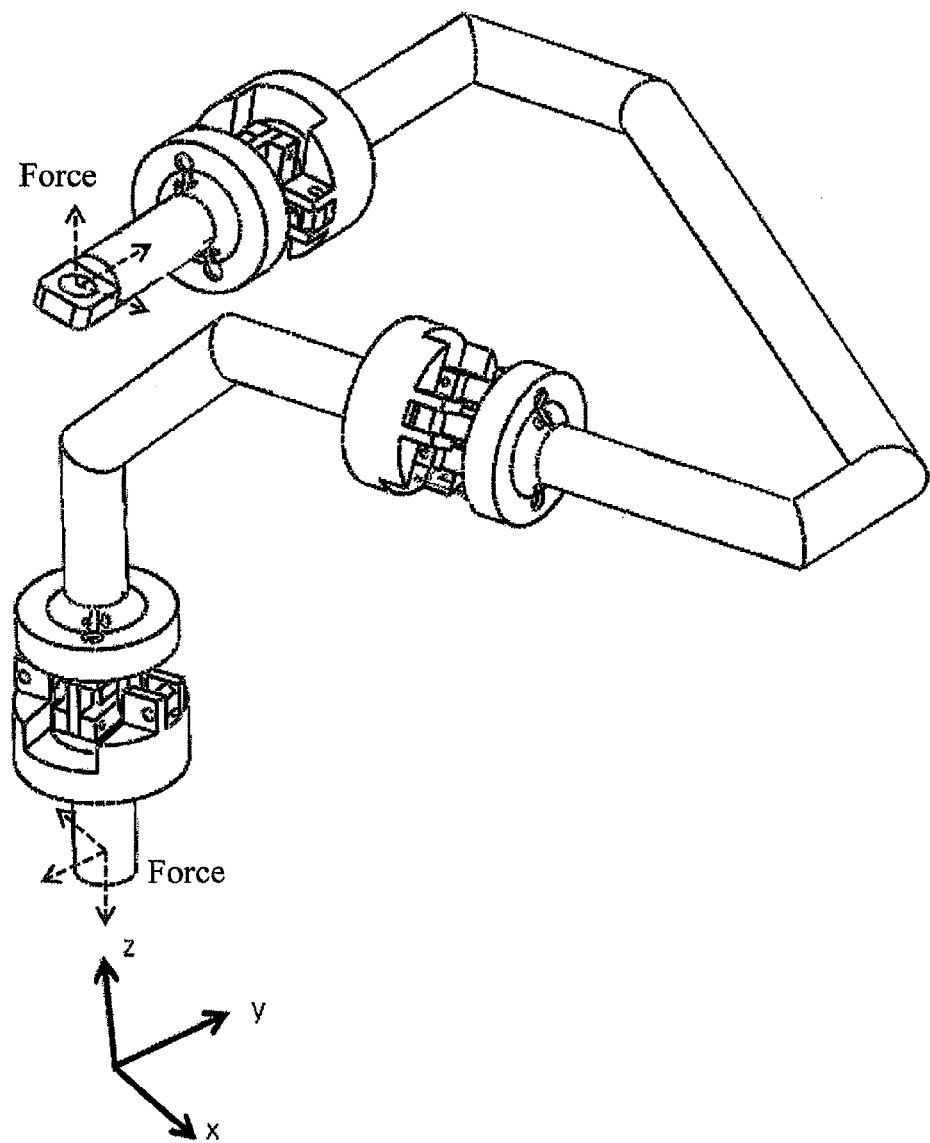

Further embodiments can combine a plurality of 2 DOF sensors according to an embodiment of the current invention to provide 4 DOF (FIG. 7A) and 6 DOF (FIG. 7B) decoupled sensors.

Figure 8A:
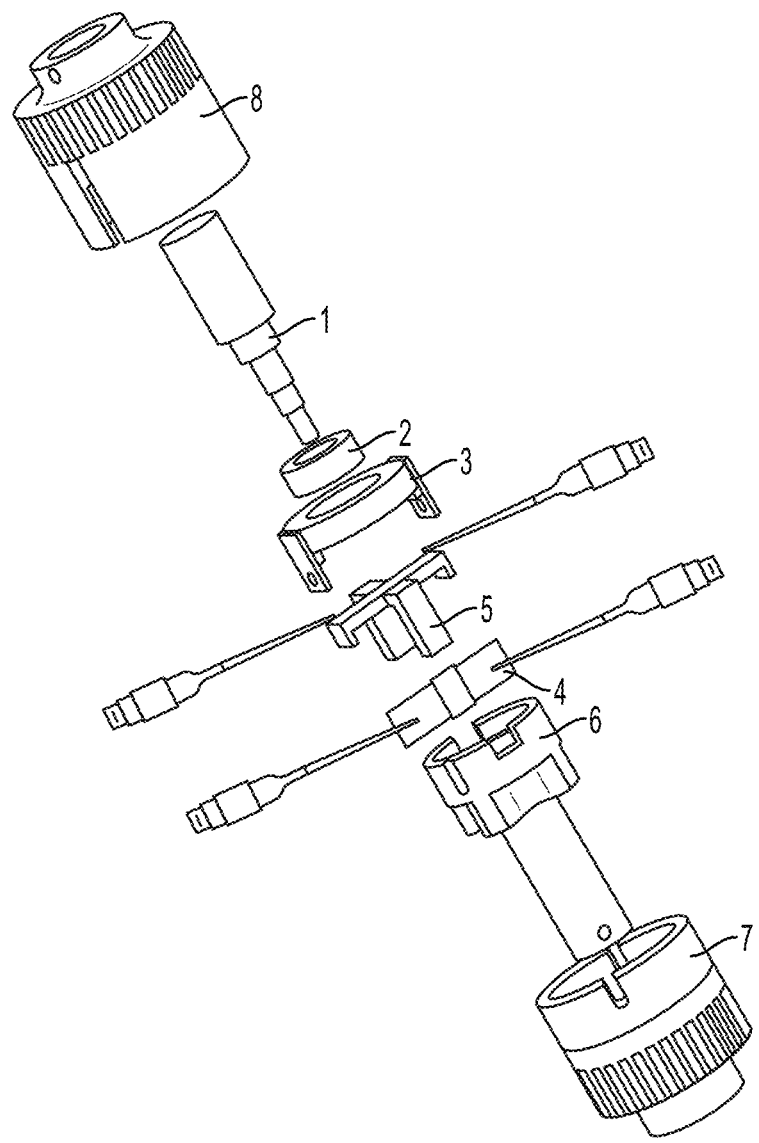
FIGS. 8A and 8B show exploded and mostly assembled views of an MRI-compatible sensor according to another embodiment of the current invention.
Figure 8B:
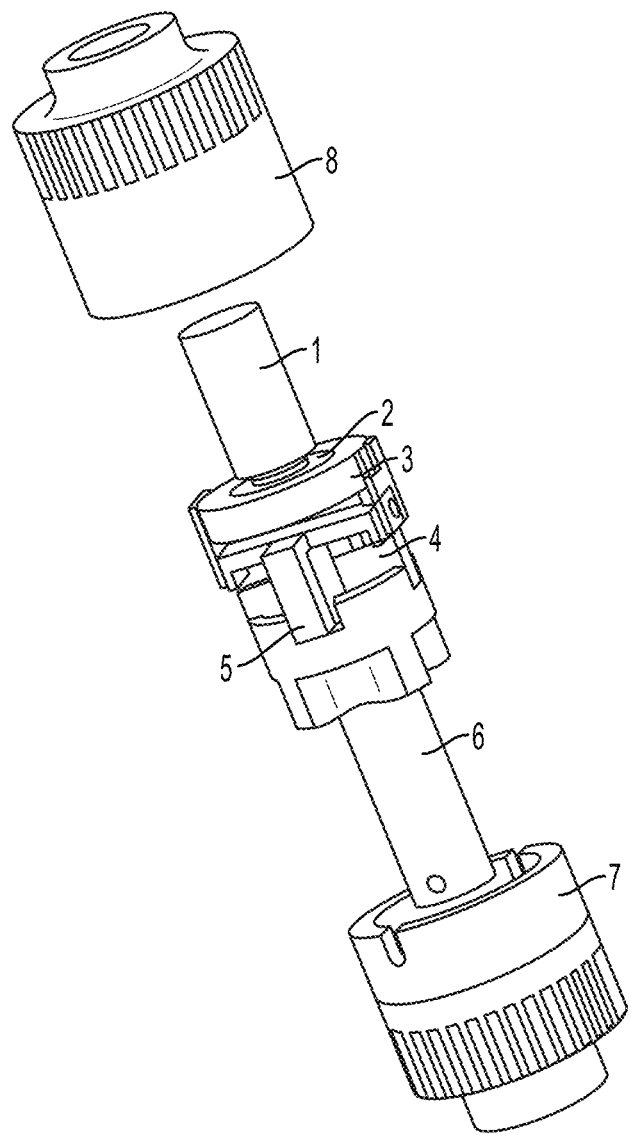

FIGS. 8A and 8B illustrate another embodiment of the current invention. In this embodiment, the FBGs are attached substantially orthogonal to the axial direction. This embodiment is thus less compact and more difficult to handle than the embodiment of FIG. 1A; however, it is also intended to be included within the broad concepts of the current invention.

Figure 9A:
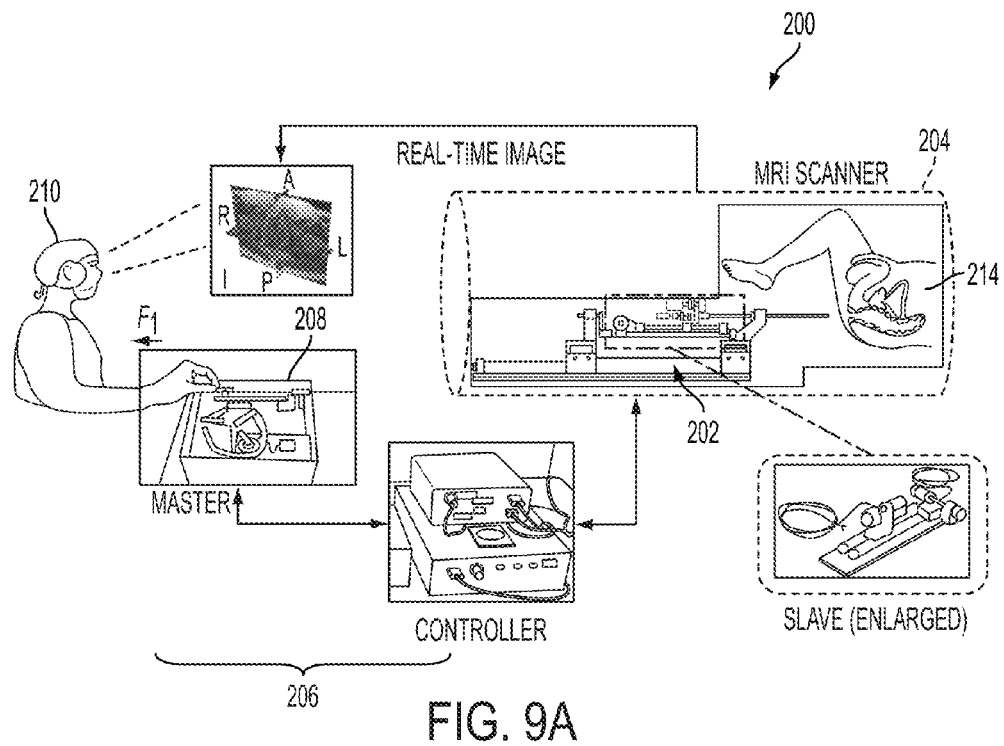
FIGS. 9A and 9B are schematic illustrations of an MRI-compatible surgical system according to another embodiment of the current invention.
Figure 9B:
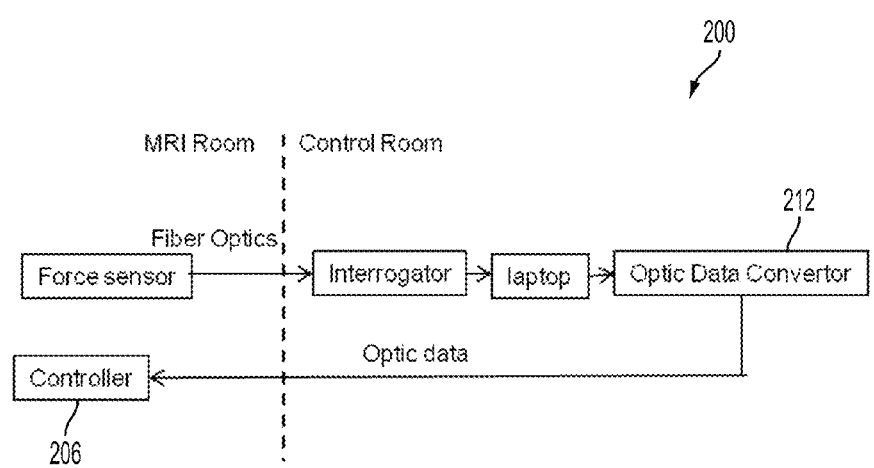

FIGS. 9A and 9B are schematic illustrations of an MRI-compatible surgical system 200 according to an embodiment of the current invention. The MRI-compatible surgical system 200 includes a teleoperated surgical tool system 202 configured to be inserted at least partially within a main coil region of an MRI system 204, and a control system 206 configured to communicate with the teleoperated surgical tool system 202. The control system includes a user interface 208 for manual input from a user 210 for real-time control of the teleoperated surgical tool system 202 during imaging of a subject with the MRI system 204. The MRI-compatible surgical system 200 also includes a signal processing system 212 configured to communicate with the control system 206 during imaging of a subject 214 with the MRI system 204. At least one of the teleoperated surgical tool system 202 or the control system 206 includes an MRI-compatible sensor for measuring torque with respect to an axis of rotation in conjunction with, and substantially independently of, an applied linear force. The MRI-compatible sensor is an MRI-compatible sensor according to an embodiment of the current invention, for example, but not limited to, MRI-compatible sensor 100. The signal processing system 212 can be located external to a Faraday cage shielding the MRI system 204 and can be configured to communicate with the control system 206 with an optical communications connection in some embodiments. In some embodiments, the optical communications connection can be a fiber optic communications system.

In some embodiments, the control system 206 includes the MRI-compatible sensor integrated into the user interface 208 to sense manual input from the user 210 while the user 210 and the control unit 206 are located inside the Faraday cage.

In some embodiments the teleoperated surgical tool system 202 includes a second MRI-compatible sensor according to an embodiment of the current invention configured to communicate with the signal processing system 212 to provide real-time feedback to the user 210 concerning at least one of a torque or force measurement of a surgical tool during use. The real-time feedback can be, or include, haptic feedback to the user interface 208. The second MRI-compatible sensor can be configured to communicate with the signal processing system 212 with an optical communications connection, which can be, a fiber optic communications system.

The following examples describe some embodiments and some applications in more detail. However, the broad concepts of the current invention are not limited to the particular examples.

EXAMPLES

Prior to the current invention, there had been a lack of a suitable, compact 2DOF sensor for force/torque sensing for prostate intervention by a master-slave system. In an embodiment of the current invention, we provide FBG sensors as the strain measuring elements. FBG is a type of distributed Bragg grating constructed in a short segment of an optical fiber that reflects a particular wavelength of light and transmits all others [13]. If the FBG experiences strain, which can be caused either by mechanical stress or thermal stress (i.e. external force/torque or temperature change), the distance between consecutive layers changes, resulting in the shift of the reflected wavelength. This wavelength shift is a linear function of both the mechanical and thermal strain. Previously, FBGs were used for needle shape tracking [14] and force measurement applied to the needle tip in retinal surgery [12]. However, no force/torque sensor with FBGs has yet been reported. Advantages of FBG sensors can include: 1) they can measure a very high strain up to 5000 (even 10000) µm/m and therefore, they can offer a higher sensitivity; 2) they are bio-compatible; 3) they are sterilizable; 4) and they are easy to install.

Since the optical fibers are utilized not only for strain measurement, but also for data transformation, they do not interfere with the MRI machine's magnetic field in any way. The interrogator (which is the signal analyzer device, generates the light and computes the wavelength shift based on the reflected signal) is placed outside the MRI room, thus it has no impact on MRI image (FIG. 9B). The calibration matrices are then applied to the wavelength shift reading on a laptop next to the interrogator in order to generate the force data. The controller software is installed on the same laptop. Force measurements are then input to the controller software to produce the control law which will be sent to the master and slave robots through the optical data convertor. This procedure ensures no interference of the force sensing with MRI since it requires no electric signal transmission.

The following criteria were considered while designing the mechanical structure of a sensor according to an embodiment of the current invention: 1) Decoupled sensor: This can simplify the calibration procedure for the sensor. This criterion is fulfilled by utilizing a ball bearing and square cross section shaft to separate axial force and axial torque flow according to an embodiment of the current invention. 2) Small size sensor: This can be necessary for the placement of the sensor in the intervention device. This criterion is considered by compact mechanical design and utilizing of FBGs with 2 mm active length as the sensing element. 3) Limitations of FBG installation: There are a few limitations which should be considered while designing the sensor, i.e. FBG curvature limitation: The FBG is embedded in a fiber and should not be overbent and Beam-to-FBG length ratio: There are some specific FBGs with standard active lengths available in the market. In this design, FBGs with 2 mm active length are selected as sensing elements. There is no standard for beam to FBG length ratio, but due to the stress concentration on the two extremities of the beam in which the FBG are installed and to avoid the effect of this inconsistency on the BFG performance, beam-to-FBG length ratio should be larger than 1. In our design 2 was selected. The FBG active length and the beam-to-FBG length ratio directly affect the size of the sensor and determine how small the sensor could be. 4) No hysteresis and no fatigue: Hysteric behavior is one of the probable problems which could be encountered in the sensor development. This problem is caused by the material used for the active elements. Basically, some of the materials have hysteric behavior. On the other hand, it should be noted that the active element is exposed to dynamic loading and unloading that could result in fatigue and failure of the sensor. In our design, phosphor bronze was considered as the material for active elements due to its hysteresis-free characteristic and high strength against dynamic loading and fatigue. Beside these advantages of the phosphor bronze, this material shows a good machinability, making the fabrication easy. 5) Temperature compensation: FBGs are very sensitive to the temperature variation. To deal with this problem, a set of two FBGs are used for each DOF. Using two FBGs and considering differential calculation, the temperature variation effect has been completely compensated.

In this section, two different decoupled designs are compared (FIGS. 1A-1C and FIGS. 8A-8B). FIG. 1A and FIG. 8A show the exploded views of the designs and where the FBGs are installed. As shown in these figures, four FBGs are used for a 2DOF sensor. Two FBGs are used for each DOF to compensate for temperature changes. The embodiment of FIG. 1A is discussed in detail above. In FIGS. 8A and 8B, parts 1 and 6 are the two ends of the sensor to connect the sensor to the test bed. Part 2 is a ball bearing and is used to decouple the force and torque making it possible to measure them independently. Part 3 exerts the axial force to the corresponding FBGs. Part 4 has a square hole in the center which transmits torque but not the axial load. In the design of FIGS. 8A and 8B), FBGs for axial force measurement are installed on part 5 while FBGs measuring the torque are installed on part 4.

Mechanical decoupling of the sensor simplifies calibration of the sensor since the calibration matrix becomes diagonal in this case:

$$\begin{bmatrix} \Delta\lambda_1 \\ \Delta\lambda_2 \end{bmatrix} = \overbrace{\begin{bmatrix} c11 & 0 \\ 0 & c22 \end{bmatrix}}^{C} \begin{bmatrix} f_z \\ \tau_z \end{bmatrix} \quad (1)$$

where C is the calibration matrix. Each element of this matrix could be found independently. $f_z$ and $\tau_z$ are the axial force and torque, respectively. $\Delta\lambda_1$ and $\Delta\lambda_2$ are the wavelength shifts of the force and torque active elements, respectively.

The functionality of both proposed designs are the same. However, in the design of FIG. 1A, the FBGs are installed axially rather than radially. This design can be advantageous to our application since it makes handling of the sensor easier and prevents the FBGs from damage.

Figure 2A:
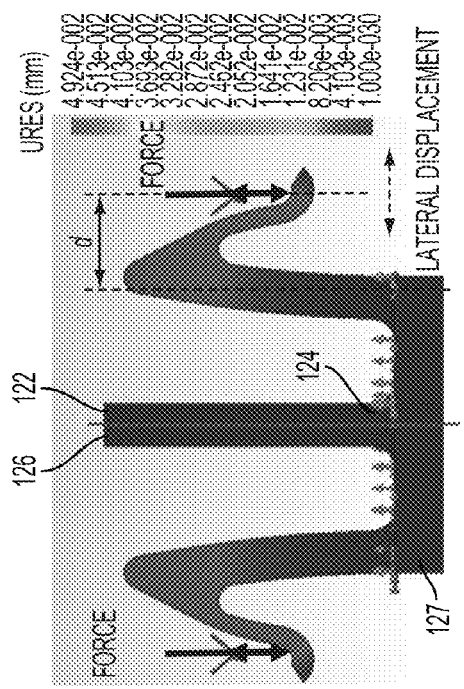
FIG. 2A is an enlarged view of a component shown in FIG. 1A.
Figure 3A:
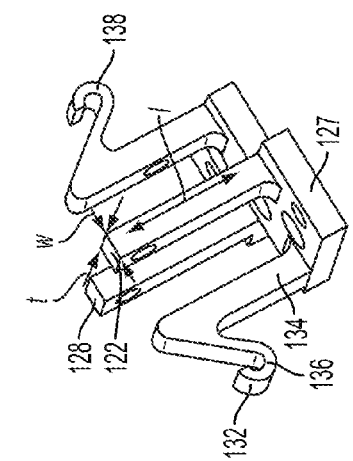
FIG. 3A shows stress distribution when a single part is used for torque transfer.

Active element 127, FIG. 2A, is made of phosphor-bronze which is a MRI-compatible material and has hysteresis free behavior. The Elasticity module is $E=1.1\times10^{11} N/m^2$. The force range of −20 to +20N and torque range of −200 to 200 Nmm are considered as the working ranges of the sensor; the resolution is considered to be 0.1 N and 1 Nmm, respectively. The strain range of 5 to 1000με is selected for the FBG sensor. Considering the desired forces and strains, the thickness and the lengths of the beams could be designed using the following equation:

$$\epsilon = \frac{3FL}{2Et^2w} \quad (2)$$

where F is the force applied to the end of the beam, L is the length of the beam, E is the Elasticity module, t and w are the thickness and width of the beam, respectively. According to equation (2), the following values yield: L=4 mm, t=1 mm and w=2 mm. FIG. 3A shows these parameters on the active element.

Finite Element Analysis

Figure 2B:
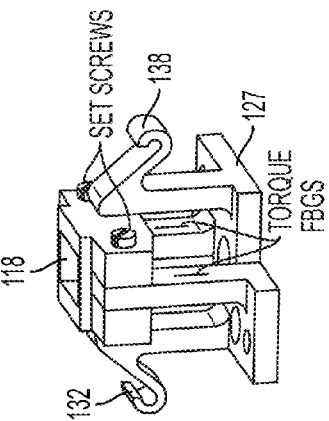
FIG. 2B shows FE results for axial force deformation of the component of FIG. 2A. Simulation shows that the tips of the L-shaped beams do not move in lateral direction, i.e. the arm d remains constant after applying the force.

Finite element (FE) analysis is used to investigate the strengths as well as linear behavior of the part on which the FBGs are installed (i.e. active elements). FIG. 2B illustrates FE results for the torsional levers when axial force is exerted on the sensor (FIG. 1A). FIG. 2A shows the location for installing FBGs for axial load. The results show that actual stress is below the yield stress (FIG. 2B). Since axial force causes bending of the active elements (the beams on which FBGs are installed), it is important to keep the arm d in FIG. 2B constant and to prevent the lateral displacement of the applied force which will cause inaccuracy in force measurement. Therefore, the beams were designed to have that specific shape as shown in FIG. 2B. Simulation results confirm negligible lateral displacement.

Figure 3B:
FIG. 3B shows stress distribution when two separate parts are used for torque transfer.
Figure 3C:
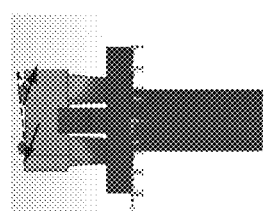
FIG. 3C is a partially assemble view of torque sensor components shown in FIG. 1A.

FIG. 3A shows why parts 118 and 127 were designed not to be a single piece. As seen, because of torsion, the gradient of stress varies in the lateral direction as well as longitudinal direction, which is not proper for the beam on which the FBGs will be installed. The stress distribution along the beam is shown in FIG. 3B when part 118 and part 127 are connected using four set screws to apply concentrated force in contact points (FIG. 3C).

SENSOR Fabrication and FBG Installation

Since our sensor is not a rigid structure and a simple calibration procedure is sought for sensor calibration due to the decoupled structure of the sensor, the dimensional and geometrical tolerances of the parts after fabrication could affect the performance of the sensor. Therefore, a precise fabrication technology should be used, especially for the active element. The active element (FIG. 2A) is manufactured by Wire EDM machine after redesigning of the part and dividing the active part to five different pieces.

Figure 4:
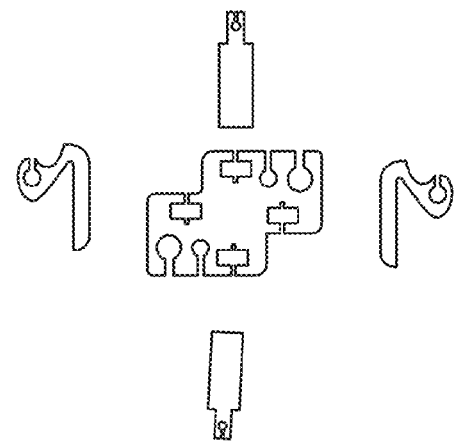
FIG. 4 shows separate pieces of to be assembled for the component of FIG. 2A which were fabricated by Wire EDM and were subsequently glued to each other.
Figure 5A:
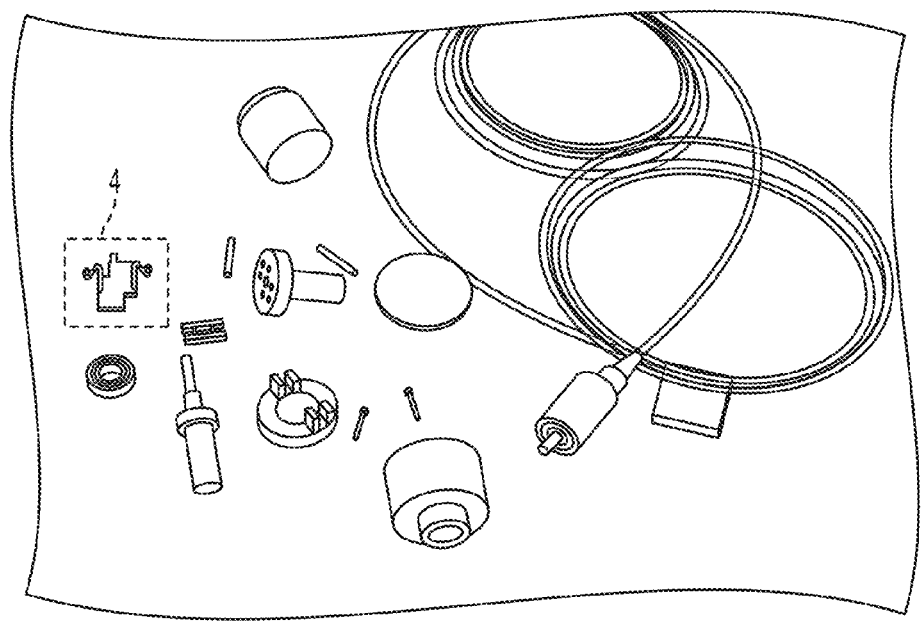
FIG. 5A shows separate pieces of an MRI-compatible sensor according to an embodiment of the current invention.

FIG. 4 illustrates five different pieces of the active element 127 which were cut by Wire EDM machine and then were attached using high strength (2600 psi) plastic steel epoxy (ITW Devcon, Danvers, Mass.) to make an integrated part. FIG. 5A shows an exploded view of the final parts. For the active element, phosphor bronze was used. Other metallic parts were made of brass. The casings were made of ABS material using rapid prototyping U print machine.

Figure 5B:
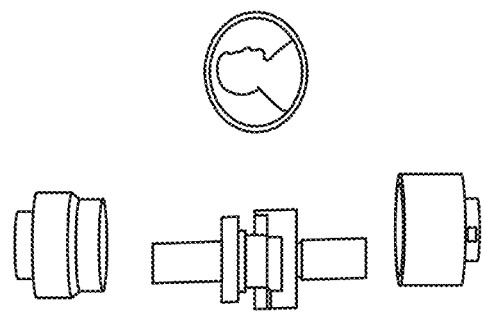
FIG. 5B shows an example of an assembled MRI-compatible sensor, without FBGs and corresponding optical fibers, according to an embodiment of the current invention.
Figure 6:
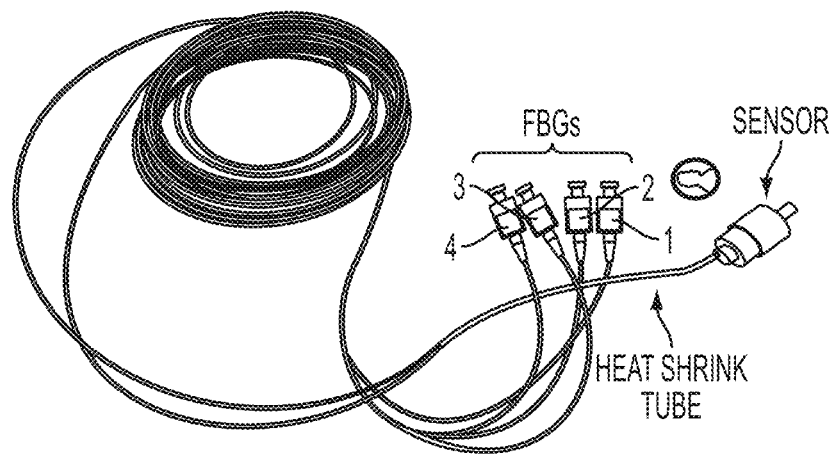
FIG. 6 shows an example of an assembled MRI-compatible sensor, including the FBGs and corresponding optical fibers, according to an embodiment of the current invention.

The ball bearing is a ceramic ball bearing which is nonmetallic and MRI-compatible. FIG. 5B demonstrates the fabricated and assembled sensor. FIG. 5B shows that the size of our sensor is small. FIG. 6 shows the final sensor with four FBGs which is ready to be plugged into the interrogator for calibration.

The proper design of the sensor and placement of the FBGs have simplified the handling of the sensor since fibers are well secured using heat shrink tubes (FIG. 6).

SENSOR Calibration and Results

Figure 10A:
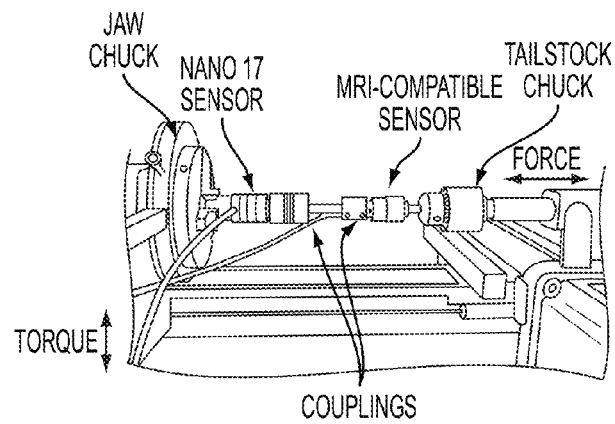
FIGS. 10A and 10B show a calibration setup for calibrating an MRI-compatible sensor according to another embodiment of the current invention.

Our sensor is fully and structurally decoupled and as a result it is very easy to be calibrated compared to other sensors. A small size lathe (Model 4410, Sherline Products, Inc., Vista, Calif.) was used to calibrate the sensor. We needed two DOFs for our calibration setup, one axial motion and one axial rotation to apply axial force and torque to the sensor. As shown in FIG. 10A, a commercial 6DOF Nano 17 sensor (ATI Industrial Automation, Apex, N.C.) was used for calibration. Nano 17 sensor and our MRI-compatible sensor were attached in series by using a flexible coupling. This set of sensors is fixed to the lathe machine between lathe jaw chuck and tailstock chuck as an integrated part. Then it was possible to apply torque to the sensors by applying torque to the jaw chuck and to apply axial force by moving the tailstock chuck in the lathe's axial direction by rotating the hand wheel.

Figure 10B:
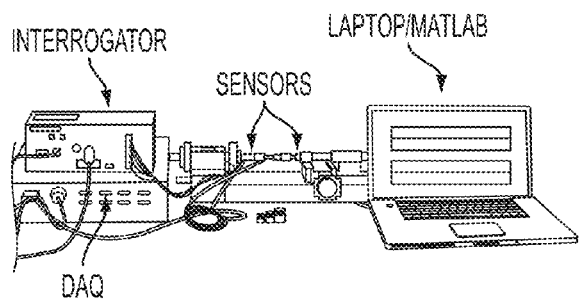

FIG. 10B shows the complete setup for our sensor calibration procedure. FBGs are connected to the interrogator (sm 130, Micron Optics, Inc., Atlanta, Ga.) and the interrogator is connected to the laptop/Matlab via network connection port and UDP protocol. The Nano 17 sensor was connected to the laptop/Matlab via a Galil controller DAQ (DB 28040, Galil Motion Control, Rocklin, Calif.). The outputs of both, the Nano 17 sensor and MRI-compatible sensor, were processed in Matlab software to estimate the calibration matrix.

For calibration of the axial force, we used the hand wheel to move the tailstock chuck and to increase the axial force gradually. The output of the Nano 17 sensor was plotted versus $\Delta\lambda_1$. The slope of the calibration line obtained was considered as the calibration coefficient, i.e. FMRI Sensor=$C_1 . \Delta\lambda_1$, where $C_1$ is the above-mentioned coefficient. The same procedure was conducted for the calibration of the axial torque.

Figure 11A:
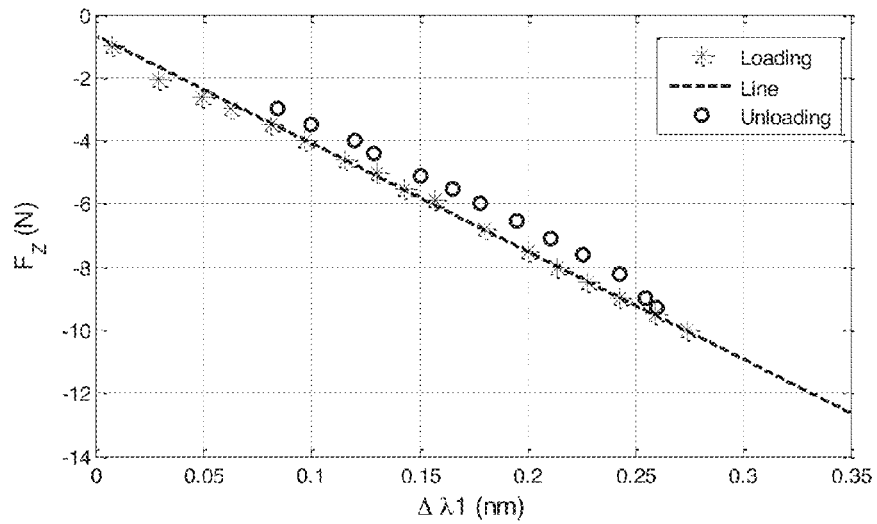
FIG. 11A shows an example of sensor calibration results for axial force for an MRI-compatible sensor according to an embodiment of the current invention.
Figure 11B:
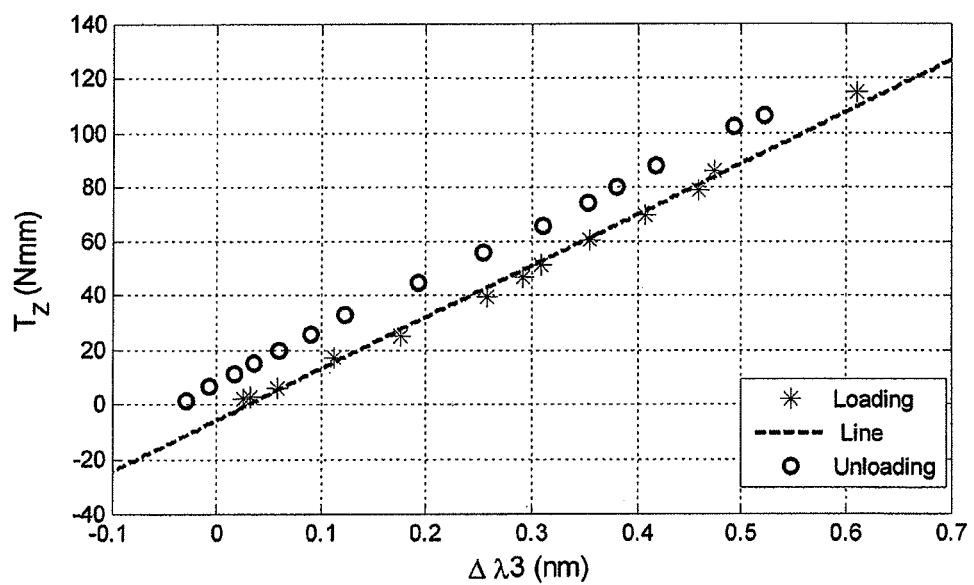
FIG. 11B shows an example of sensor calibration results for axial torque for an MRI-compatible sensor according to an embodiment of the current invention.

For this case, a range of standard weights were used to apply torque on the jaw chuck by an extended arm. The axial force and torque were applied in both directions. FIGS. 11A and 11B show the calibration results for the axial force and axial torque, respectively.

Results (FIGS. 11A and 11B) show linear behavior of the sensor for axial force and axial torque loading and unloading. In these figures, there are some shifts between loading and unloading both in axial force and axial torque. These shifts are caused because of several reasons: 1) installation of the FBGs on two beams instead of four beams that caused asymmetric structure and made the sensor sensitive to lateral force and force distribution, 2) manufacturing errors especially an undesired clearance between shaft 102 and base 104 (FIG. 1A) which caused undesired sensitivity of the sensor to lateral forces, and 3) the assembling inaccuracy of the sensors in the calibration setup which could cause lateral forces.

CONCLUSIONS

A structurally inherent decoupled MRI force/torque sensor was designed, fabricated and calibrated to be used in a master-slave needle steering procedure under real-time MRI utilizing Fiber Bragg Grating technology. A structurally decoupled sensor prevents interference of force and torque in different directions, thus it was easier to calibrate and it provides better accuracy. The calibration results show linear behavior of the sensor, but it also demonstrates a shift in the diagram in loading and unloading which was due to manufacturing errors and calibration setup and will be addressed in alternative embodiments.

REFERENCES

[1] Seifabadi, R., Iordachita, I., and Fichtinger, G., "Design of a teleoperated needle steering system for MRI-guided prostate interventions". 4th IEEE RAS & EMBS International Conference on Biomedical Robotics and Biomechatronics (BioRob), 793-798 (2012)

[2] Seifabadi, R., Cho, N. B., Song, S. E., Tokuda, J., Hata, N., Tempany, C. M., and Iordachita, I. "Accuracy study of a robotic system for MRI-guided prostate needle placement", International Journal of Medical Robotics and Computer Assisted Surgery, 7(2), 181-190, (2012).

[3] Tokuda, J., Song, S. E., Fischer, G. S., Iordachita, I. I., Seifabadi, R., Cho, N. B., and Hata, N., "Preclinical evaluation of an MRI-compatible pneumatic robot for angulated needle placement in transperineal prostate interventions," Int JCARS, 7(6), 949-957, (2012).

[4] Su, H., and Fischer, G. S., "A 3-Axis Optical Force/Torque Sensor for Prostate Needle Placement in Magnetic Resonance Imaging Environments," IEEE International Conference on Technologies for Practical Robot Applications, 5-9 (2009).

[5] Tada, M., Sasaki, S., and Ogasawara, T., "Development of an optical 2-axis force sensor usable in MRI environments," Proc. of the IEEE Sensors, 2, 984-989 (2002).

[6] Chapuis, D., Gassert, R., Sache, L., Burdet, E., and Bleuler, H., "Design of a Simple MRI/fMRI Compatible Force/Torque Sensor," Proceedings of 2004 IEEE/RSJ International Conference on Intelligent Robots and Systems, 3, 2593-2599 (2004).

[7] Tada, M., and Kanade, T., "Design of an MR-compatible three-axis force sensor," IEEE/RSJ International Conference on Intelligent Robots and Systems, 3505-3510 (2005).

[8] Tokuno, T., Tada, M., and Umeda, K., "High-Precision MRI-Compatible Force Sensor with Parallel Plate Structure," Proceedings of the 2nd Biennial IEEE/RAS-EMBS International Conference on Biomedical Robotics and Biomechatronics, 33-38 (2008).

[9] Puangmali, P., Althoefer, K., and Seneviratne, L. D., "Novel Design of a 3-Axis Optical Fiber Force Sensor for Applications in Magnetic Resonance Environments," IEEE International Conference on Robotics and Automation, 3682-3687 (2009).

[10] Polygerinos, P., Puangmali, P., Schaeffter, T., Razavi, R., Seneviratne, L. D., and Althoefer, K., "Novel Miniature MRI-Compatible Fiber-Optic Force Sensor for Cardiac Catheterization Procedures," IEEE International Conference on Robotics and Automation, 2598-2603 (2010).

[11] Tan, U., Yang, B., Gullapalli, R., and Desai, J. P., "Tri-axial MRI-Compatible Fiber-optic Force Sensor," IEEE Transactions on Robotics, 27(1), 65-74 (2011).

[12] Iordachita, I., Sun, Z., Balicki, M., Kang. J. U., Phee, S. J., Handa, J., Gehlbach., P., and Taylor, R., "A sub-millimetric, 0.25 mN resolution fully integrated fiber-optic force-sensing tool for retinal microsurgery," Int J CARS, 4(4), 383-390 (2009).

[13] Hill, K. O., and Meltz, G., "Fiber Bragg grating technology fundamentals and overview," Journal of Lightwave Technology, 15(8), 1263-1276 (1997).

[14] Yong-Lae, P., Elayaperumal, S., Daniel, B., Ryu, S. C., Shin, M., Savall, J., Black R. J., Moslehi, B., and Cutkosky, M. R. "Real-Time Estimation of Three-Dimensional Needle Shape and Deflection for MRI-Guided Interventions," IEEE/ASME Trans. Mechatronics-Focused Section on Surgical and Interventional Medical Devices, 15(6), 906-915 (2010).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A magnetic resonance imaging (MRI) compatible sensor for measuring torque with respect to an axis of rotation in conjunction with an applied linear force, comprising:

a shaft arranged in a longitudinal direction substantially along said axis of rotation;

a base component arranged along said axis of rotation and displaced with respect to said shaft;

a torque detector assembly configured to be coupled to rotational motion of said shaft about said axis of rotation relative to said base component; and a linear-force detector assembly configured to be coupled to linear motion of said shaft from a force applied in a direction substantially coincident with said axis of rotation relative to said base component, wherein said torque detector assembly and said linear-force detector assembly are substantially de-coupled from each other such that torque measurements are substantially independent of linear force measurements, and
wherein said MRI compatible sensor consists essentially of MRI compatible materials.

2. The MRI compatible sensor according to claim 1, wherein said torque detector assembly comprises a first fiber-optic strain sensor element, and
wherein said linear-force detector assembly comprises a second fiber-optic strain sensor element.

3. The MRI compatible sensor according to claim 2, wherein said torque detector assembly comprises a third fiber-optic strain sensor element arranged relative to said first fiber-optic strain sensor element to provide substantially temperature-independent torque measurements, and
wherein said linear-force detector assembly comprises a fourth fiber-optic strain sensor element arranged relative to said second fiber-optic strain sensor element to provide substantially temperature-independent linear force measurements.

4. The MRI compatible sensor according to claim 3, wherein each of said first, second, third and fourth fiber-optic strain sensors is an optical fiber comprising a Fiber Bragg Grating (FBG) section.

5. The MRI compatible sensor according to claim 1, wherein said torque detector assembly comprises a rotational engaging component configured to couple to said shaft while said shaft is subjected to a torque along said axis of rotation,
wherein said torque detector assembly further comprises a flexural beam having a first end fixed relative to said base component and an end free to move relative to said base component, and
wherein said rotational engaging component is arranged to come into contact with said flexural beam to change an amount of force imposed on said flexural beam responsive to said torque along said axis of rotation.

6. The MRI compatible sensor according to claim 5, wherein said torque detector assembly further comprises a first fiber-optic strain sensor element attached along a first side of said flexural beam to be responsive to changes in strain resulting from changes in said amount of force imposed on said flexural beam.

7. The MRI compatible sensor according to claim 6, wherein said torque detector assembly further comprises a second fiber-optic strain sensor element attached along a second side of said flexural beam to be responsive to changes in strain resulting from changes in said amount of force imposed on said flexural beam such that changes in strain on said second fiber-optic strain sensor element are opposite in sign relative to changes in strain on said first fiber-optic strain sensor element to provide substantially temperature-independent torque measurements.

8. The MRI compatible sensor according to claim 7, wherein said linear-force detector assembly comprises a force-transfer component configured to couple to said shaft while said shaft is subjected to a force along said axis of rotation,
wherein said linear-force detector assembly further comprises a flexural lever having a first end fixed relative to said base component and an end free to move relative to said base component, and
wherein said force-transfer component is arranged to come into contact with said flexural lever to change an amount of force imposed on said flexural lever responsive to said force along said axis of rotation.

9. The MRI compatible sensor according to claim 8, wherein said force-transfer component comprises rotational slip joint, and
wherein said shaft passes through said rotational slip joint such that rotations of said shaft are substantially frictionless so that substantially no torque is transmitted from said shaft to said force-transfer component.

10. The MRI compatible sensor according to claim 9, wherein said rotational slip joint is a ball bearing assembly.

11. The MRI compatible sensor according to claim 8, wherein said linear-force detector assembly further comprises a third fiber-optic strain sensor element attached along a first side of said flexural lever to be responsive to changes in strain resulting from changes in said amount of force imposed on said flexural lever.

12. The MRI compatible sensor according to claim 11, wherein said linear-force detector assembly further comprises a fourth fiber-optic strain sensor element attached along a second side of said flexural lever to be responsive to changes in strain resulting from changes in said amount of force imposed on said flexural lever such that changes in strain on said fourth fiber-optic strain sensor element are opposite in sign relative to changes in strain on said third fiber-optic strain sensor element to provide substantially temperature-independent force measurements.

13. The MRI compatible sensor according to claim 12, wherein each of said first, second, third and fourth fiber-optic strain sensors is an optical fiber comprising an FBG section.

14. The MRI-compatible surgical system, comprising:
a teleoperated surgical tool system configured to be inserted at least partially within a main coil region of an MRI system;
a control system configured to communicate with said teleoperated surgical tool system, said control system comprising a user interface for manual input from a user for real-time control of said teleoperated surgical tool system during imaging of a subject with said MRI system; and
a signal processing system configured to communicate with said control system during imaging of a subject with said MRI system,
wherein at least one of said teleoperated surgical tool system or said control system comprises an MRI-compatible sensor for measuring torque with respect to an axis of rotation in conjunction with, and substantially independently of, an applied linear force.

15. The MRI-compatible surgical system according to claim 14, wherein said signal processing system is located external to a Faraday cage shielding said MRI system and is configured to communicate with said control system with an optical communications connection.

16. The MRI-compatible surgical system according to claim 15, wherein said optical communications connection is a fiber optic communications system.

17. The MRI-compatible surgical system according to claim 16, wherein said control system comprises said MRI-compatible sensor integrated into said user interface to sense manual input from said user while said user and said control unit are located inside said faraday cage.

18. The MRI-compatible surgical system according to claim 17, wherein said teleoperated surgical tool system comprises a second MRI-compatible sensor configured to communicate with said signal processing system to provide real-time feedback to said user concerning at least one of a torque or force measurement of a surgical tool during use.

19. The MRI-compatible surgical system according to claim 18, wherein said real-time feedback comprises haptic feedback to said user interface.

20. The MRI-compatible surgical system according to claim 18, wherein said second MRI-compatible sensor is configured to communicate with said signal processing system with an optical communications connection.

21. The MRI-compatible surgical system according to claim 20, wherein said optical communications connection is a fiber optic communications system.

22. The MRI-compatible surgical system according to claim 14, wherein said MRI-compatible sensor comprises:
 a shaft arranged in a longitudinal direction substantially along said axis of rotation;
 a base component arranged along said axis of rotation and displaced with respect to said shaft;
 a torque detector assembly configured to be coupled to rotational motion of said shaft about said axis of rotation relative to said base component; and
 a linear-force detector assembly configured to be coupled to linear motion of said shaft from a force applied in a direction substantially coincident with said axis of rotation relative to said base component,
 wherein said torque detector assembly and said linear-force detector assembly are substantially de-coupled from each other such that torque measurements are substantially independent of linear force measurements, and
 wherein said MRI compatible sensor consists essentially of MRI compatible materials.

23. The MRI-compatible surgical system according to claim 22, wherein said torque detector assembly comprises a first fiber-optic strain sensor element, and
 wherein said linear-force detector assembly comprises a second fiber-optic strain sensor element.

24. The MRI-compatible surgical system according to claim 23, wherein said torque detector assembly comprises a third fiber-optic strain sensor element arranged relative to said first fiber-optic strain sensor element to provide substantially temperature-independent torque measurements, and
 wherein said linear-force detector assembly comprises a fourth fiber-optic strain sensor element arranged relative to said second fiber-optic strain sensor element to provide substantially temperature-independent linear force measurements.

25. The MRI-compatible surgical system according to claim 24, wherein each of said first, second, third and fourth fiber-optic strain sensors is an optical fiber comprising a FBG section.

* * * * *